United States Patent [19]

Duckworth

[11] Patent Number: 4,927,625
[45] Date of Patent: May 22, 1990

[54] TOOTHPASTES

[75] Inventor: Ralph M. Duckworth, Kelsall, England

[73] Assignee: Lever Brothers Company, New York, N.Y.

[21] Appl. No.: 233,693

[22] Filed: Aug. 18, 1988

[30] Foreign Application Priority Data

Aug. 21, 1987 [GB] United Kingdom ............... 8719775

[51] Int. Cl.$^5$ .................... A61K 7/16; A61K 7/18
[52] U.S. Cl. ........................... 424/52; 424/40
[58] Field of Search ...................... 424/52, 49

[56] References Cited

U.S. PATENT DOCUMENTS

| Patent No. | Date | Inventor | Class |
|---|---|---|---|
| 2,901,400 | 8/1959 | Thomas | 424/52 |
| 3,012,852 | 12/1961 | Nelson | 23/109 |
| 3,119,743 | 1/1964 | Ericson | 424/52 |
| 3,227,617 | 1/1966 | Manahan et al. | 424/52 |
| 3,227,618 | 1/1972 | Manahan et al. | 424/52 |
| 3,378,445 | 4/1968 | Muhler | 424/52 |
| 3,450,813 | 6/1969 | Muhler | 424/52 |
| 3,538,230 | 11/1970 | Pader et al. | 424/52 |
| 3,634,585 | 1/1972 | Manahan et al. | 424/52 |
| 3,662,059 | 5/1972 | Wiesner et al. | 424/52 |
| 3,678,155 | 7/1972 | Clippingdale et al. | 424/52 |
| 3,689,637 | 9/1972 | Pader | 424/52 |
| 3,703,583 | 11/1972 | Martin | 424/54 |
| 3,793,447 | 2/1974 | De Palma et al. | 424/54 |
| 3,822,345 | 7/1197 | Murray et al. | 424/52 |
| 3,864,471 | 2/1975 | King et al. | 424/52 |
| 3,914,406 | 10/1975 | Yankell | 424/52 |
| 3,941,877 | 5/1976 | King et al. | 424/52 |
| 3,956,478 | 5/1976 | King et al. | 424/52 |
| 4,025,616 | 5/1977 | Haefele | 424/52 |
| 4,096,241 | 6/1978 | Geistlich et al. | 424/54 |
| 4,100,269 | 7/1978 | Pader | 424/59 |
| 4,141,969 | 2/1979 | Mitchell | 424/52 |
| 4,233,288 | 11/1980 | Cornell | 424/48 |
| 4,556,553 | 6/1976 | Suganuma et al. | 424/52 |
| 4,645,662 | 2/1987 | Nakashima et al. | 424/58 |
| 4,689,216 | 8/1987 | Greene | 424/58 |

FOREIGN PATENT DOCUMENTS

| Number | Date | Country | Class |
|---|---|---|---|
| 207489 | 4/1957 | Australia | 424/52 |
| 974453 | 9/1975 | Canada | 424/52 |
| 0002386 | 6/1979 | European Pat. Off. | 424/52 |
| 0008480 | 3/1980 | European Pat. Off. | |
| 0216189 | 8/1986 | European Pat. Off. | |
| 0227108 | 7/1987 | European Pat. Off. | |
| 907417 | 10/1962 | United Kingdom | |
| 999857 | 7/1965 | United Kingdom | |
| 1132830 | 12/1968 | United Kingdom | |
| 1365296 | 8/1974 | United Kingdom | 424/52 |
| 1384375 | 2/1975 | United Kingdom | |
| 1535031 | 12/1978 | United Kingdom | |
| 2001849 | 2/1979 | United Kingdom | |
| 1572164 | 7/1980 | United Kingdom | |
| 2160098 | 12/1985 | United Kingdom | |
| 2164255 | 3/1986 | United Kingdom | |
| 2117637 | 10/1988 | United Kingdom | |

OTHER PUBLICATIONS

Schrader's 'Grundlagen u. Rezepturen der Kosmetika', p. 415, 1979.
"Some Aspects of the Kinetics of Fluoride in Saliva", J. Ekstrand, F. Lagerloff and A. Oliveby, pp. 91–98, 1986.
J. Dent Res., 66(2): 430–435, Feb. 1987.
Derwent WPI Acc. No. 85-138981/23, Lion Corp., JPN 60075415, 4/27/85, Dentifrice . . . : "Calcium-Free Abrasive".
Derwent WPI Acc. 86-144090/22, Zetacron Inc., WO 8602831 A, 5/22/86, Keith, A., "Calcium-Free Dentifrice Compositions".

Primary Examiner—Shep K. Rose
Attorney, Agent, or Firm—Milton L. Honig

[57] ABSTRACT

The invention relates to a toothpaste containing a therapeutic agent through the use of which there is produced a sustained and enhanced level of the therapeutic agent in the oral fluids. The toothpaste comprises an abrasive cleaning agent, a therapeutic agent, 0.01 to 0.6% by weight of a flavouring agent, 0.002 to 0.1% by weight of sodium saccharinate or the equivalent amount of another sweetening agent and 0 to 1.5% by weight of an anionic surfactant.

10 Claims, No Drawings

TOOTHPASTES

This invention relates to toothpastes, more particularly toothpastes which comprise a therapeutic agent. The invention will be described with particular reference to its application to the use of fluorine-containing therapeutic agents for combating dental caries. However, it is evident that the invention is in principle applicable to the delivery in the oral cavity of other therapeutic agents. Toothpastes include both opaque products and transparent gel products but do not include prophylactic pastes.

It is well known to include water-soluble fluorine-containing salts, for example sodium fluoride or sodium monofluorophosphate, in toothpastes and that by the regular daily use of such toothpastes the incidence of dental caries can be reduced. It is believed that the fluoride ion, or monofluorophosphate ion, interacts with the tooth substance and increases its resistance to acid attack and also aids remineralisation of incipient caries lesions. However, the opportunity for this efficacious interaction to occur is short-lived because the oral fluoride level falls off rapidly after use of a mouthwash or toothpaste.

Evidence is given by Fejerskov et al (Acta Odontol. Scand., 1981, 39, 241–249) that fluoride, even in low concentrations, is necessary in the oral fluids to obtain maximum caries inhibition concluding that continuous or frequent supplementation of fluoride to oral fluids is mandatory particularly in cases of increased cariogenic challenge at any age.

Attempts have been made to provide means for maintaining a certain concentration of fluoride ions in the mouth over a longer period. These have included proposals for locating a fluoride ion source in the mouth, for example as part of an orthodontic appliance. More recently, Williams et al, Journal of Pedodontics, Spring 1982, 218–228, have disclosed adhering fluoride-containing microcapsules to teeth with guar gum to provide a sustained release source of fluoride. Spooner et al, Int. J Pharmaceutics, 15, 177–184, 1983 describe a device located at a demineralised enamel surface for the sustained release of fluoride ions which device comprises a supply of particles of calcium fluoride contained within a membrane. Ogaard et al, Caries Res., 17, 520–524, 1983 postulate that calcium fluoride formed in outer layers of tooth enamel by treatment with an aqueous solution of sodium fluoride might well serve as a significant reservoir of fluoride and may be of prime importance concerning the cariostatic effect of the retained fluoride.

In our EP-A-228 209 and EP-A-263 638 we have described other means for maintaining a certain concentration of fluoride ions in the mouth. In EP-A-228 209 a means is described for the attachment to oral surfaces of particles which slowly release a therapeutic agent, especially fluoride ions. In EP-A-263 638 the desired effect is obtained through the deposition in the mouth of particles of freshly precipitated calcium fluoride.

The present invention is based on our surprising discovery that a sustained level of therapeutic agent in the oral fluids can be obtained by the use of a toothpaste comprising a therapeutic agent which during brushing of the teeth with the toothpaste stimulates the flow of saliva substantially less than conventional products. Reduced salivary flow has the effect of lessening the dilution of the fluorine-containing or other therapeutic agent in the oral fluids and this promotes a sustained therapeutic effect.

Conventional commercial oral products contain ingredients which markedly stimulate salivary flow. In particular we have found that commonly employed ingredients which have a marked stimulatory effect on salivary flow are flavouring oils and sweetening agents. In toothpastes in accordance with this invention the amounts of these ingredients are reduced relative to the amounts used in conventional products.

It has also been discovered that a further improvement is obtained by limiting the amount of anionic surfactant that may be present in the toothpaste. Toothpastes almost invariably comprise an anionic surfactant. We have found that the presence of an anionic surfactant in a toothpaste comprising a fluorine-containing or other therapeutic agent reduces the retention of the fluorine-containing or other agent in the mouth and thereby reduces its efficacy. The exact mechanism by which a reduction in the level of the surfactant operates to give an enhanced sustained therapeutic effect is uncertain. One possible way is by modifying the impact of the flavouring oil in the mouth so as to lessen the stimulation of salivary flow.

According to the invention there is provided a toothpaste containing an abrasive cleaning agent, a therapeutic agent, 0.01 to 0.6% by weight of a flavouring agent, 0.002 to 0.1% by weight of sodium saccharinate or the equivalent amount of another sweetening agent and 0 to 1.5% by weight of an anionic surfactant.

The toothpaste of the invention includes an abrasive cleaning agent. While many abrasive agents have been proposed in the literature the silica and alumina abrasives which are in wide use are preferred. Other well known abrasives include dicalcium phosphate dihydrate, insoluble sodium metaphosphate, calcium pyrophosphate, calcium carbonate and plastics materials. Abrasive agents are usually present in toothpastes in an amount of 5 to 75% by weight.

Many therapeutic agents have been proposed for use in toothpastes for care of the oral cavity and these include salts liberating therapeutically active ions in aqueous media as well as non-ionic and cationic organic antibacterial agents.

A preferred oral therapeutic agent is a fluorine-containing compound. Examples are sodium fluoride, sodium monofluorophosphate, mixtures of sodium fluoride and sodium monofluorophosphate, and stannous fluoride. The amount of the fluorine-containing compound will generally be from 0.05 to 3% by weight, more particularly an amount sufficient to provide about 50 to 3500 ppm of ionic fluoride (e.g. $F^-$ or $FPO_3^{--}$) by weight of the toothpaste. Other fluoride salts have also been proposed as sources of ionic fluoride in the treatment of dental caries.

The use of zinc salts is disclosed in U.S. No. 4,100,269 and U.S. No. 4,022,880. Formulae which include sources of copper ions are disclosed in EP-B-38 867.

Other sources of metal ions are potassium and strontium salts which have a tooth desensitising action. Such salts are disclosed in U.S. No. 3,863,006, EP-A-95 871, WO 85/04098, U.S. No. 3,122,483 and U.S. No. 3,699,221.

Other therapeutically active ions include stannous ions and condensed phosphate ions, the latter being disclosed in U.S. No. 4,515,772 and U.S. No. 4,627,977.

A number of non-ionic organic antibacterial agents including triclosan are disclosed in EP-A-161 898. Use of triclosan is also disclosed in EP-A-161 899.

The therapeutic agent may also be casein or a casein derivative as disclosed in EP-A-166 055 and WO 82/03008.

The amount of the therapeutic agent will generally be in the range 0.1 to 8% by weight of the toothpaste.

Flavouring oils commonly used in toothpastes are peppermint oil, spearmint oil, oil of wintergreen and mixtures thereof. A number of other flavouring oils have been suggested for use in toothpastes including sassafras, clove, sage, eucalyptus, marjoram, cinnamon, lemon and orange.

In the toothpaste of this invention the amount of the flavouring agent used is 0.01 to 0.6% by weight of the toothpaste. Preferred amounts are 0.01 to 0.5% by weight with the most preferred range being 0.01 to 0.4% by weight.

Sodium saccharinate is a commonly used sweetening agent and other sweetening agents that may be used in toothpastes include aspartame, lactose, maltose, sodium cyclamate and thaumatin.

In the toothpastes of the invention the amount of sodium saccharinate used is 0.002 to 0.1%, preferably 0.002 to 0.06%, by weight, or there is employed an amount of another agent imparting equivalent sweetness.

It will be appreciated by those skilled in the art that the amounts of flavouring agent and sweetening agent used in toothpastes of this invention are substantially less than those amounts used in conventional commercial products.

The anionic surfactant most commonly used in commercial toothpastes is sodium lauryl sulphate, but other anionic surfactants have also been used and these include sodium dodecylbenzene sulphonate, sodium lauroyl sarcosinate and sodium coconut monoglyceride sulphonate. Toothpastes of this invention comprise 0 to 1.5% by weight of anionic surfactant. In preferred products the amount of anionic surfactant is 0 to 1% by weight with most preferred amounts being 0 to 0.75% by weight.

Toothpastes of this invention may include other surfactants especially non-ionic surfactants.

Toothpastes of the invention will also comprise the usual additional ingredients in particular humectant and binder or thickening agent.

Humectants which may be used include glycerol, sorbitol syrup, polyethylene glycol, lactitol, xylitol or hydrogenated corn syrup. The total amount of humectant present will generally range from 10% to 85% by weight of the toothpaste.

Numerous binding or thickening agents have been indicated for use in toothpastes, preferred ones being sodium carboxymethylcellulose and xanthan gum. Others include natural gum binders such as gum tragacanth, gum karaya and gum arabic, Irish moss, alginates and carrageenans. Silica thickening agents include the silica aerogels and various precipitated silicas. Mixtures of binders and thickening agents may be used. The amount of binder and thickening agent included in a toothpaste is generally between 0.1 and 15% by weight.

The following Examples illustrate the invention. All percentages herein are by weight.

| Ingredient | % Example No. 1 | 2 | 3 | 4 |
| --- | --- | --- | --- | --- |
| Alumina trihydrate | 50.00 | 50.00 | 50.00 | 50.00 |
| Sorbitol syrup (70% solution) | 29.50 | 29.82 | 29.685 | 29.415 |
| Sodium lauryl sulphate | 0.15 | 0.075 | 0.15 | 0.30 |
| Sodium carboxymethylcellulose | 0.85 | 1.00 | 1.00 | 1.00 |
| Sodium monofluorophosphate | 0.76 | 0.455 | 0.455 | 0.455 |
| Sodium saccharinate | 0.02 | 0.01 | 0.02 | 0.04 |
| Monosodium phosphate (anhydrous) | 0.31 | 0.31 | 0.31 | 0.31 |
| Titanium dioxide | 0.50 | 0.50 | 0.50 | 0.50 |
| Flavour (spearmint oil) | 0.10 | 0.05 | 0.10 | 0.20 |
| Water | 17.81 | 17.78 | 17.78 | 17.78 |

The toothpastes of this invention are characterised by relatively low levels of both flavouring agent and sweetening agent. Thereby when the teeth are brushed with such toothpastes there is less stimulation of saliva flow. This effect has been demonstrated by the applicants in tests using the toothpastes of Examples 1 to 4.

For each of the toothpastes there was determined their respective Relative Saliva Flow Index. This index expresses the stimulated saliva flow relative to the stimulated saliva flow during use of a standard conventional product.

The test method for the determination of the Relative Saliva Flow Index (RSFI) of the toothpastes of the above Examples will now be described.

Test Method

In this saliva flow test the panellists participate in the afternoons, i.e. after their midday meal, and they are requested not to eat or drink for at least 30 minutes before both step 1 and step 2 of the test. Excluded were panellists with an abnormally high or an abnormally low unstimulated saliva flow rate.

Step 1

A panel of 10 subjects rinse for 5 seconds with 10 ml water and expectorate, i.e. spit it out. Then after 5 mins panellists swallow, brush their teeth for 1 min using 1.5 g of standard toothpaste and collect all expectorate into a preweighed container. The container is reweighed and the weight of expectorate (W1) is obtained by difference.

Step 2

At the time of day on the next day step 1 is repeated but with the standard toothpaste replaced by the test toothpaste. The weight of expectorate from repeat step 1 is W2.

The RSFI as used herein is given by the expression $$RSFI = \frac{W2 - 1.5}{W1 - 1.5} \times 100$$

The standard toothpaste has the following composition.

| Ingredient | % |
| --- | --- |
| Alumina trihydrate | 50.00 |
| Sorbitol syrup (70% solution) | 27.00 |
| Sodium lauryl sulphate | 1.50 |
| Sodium carboxymethylcellulose | 0.85 |
| Sodium monofluorophosphate | 0.76 |
| Sodium saccharinate | 0.20 |
| Monosodium phosphate (anhydrous) | 0.31 |

-continued

| Ingredient | % |
|---|---|
| Titanium dioxide | 0.50 |
| Flavour (spearmint oil) | 1.00 |
| Water (demineralised) | to 100.00 |

The toothpastes of Examples 1 to 4 and the standard toothpaste were made in a conventional way.

In one test involving Example 1 the value of (W1-1.5) for the standard toothpaste was 3.83 (1.13), the number between brackets being the standard deviation. In a second test involving Examples 2, 3, and 4, the value of (W1-1.5) for the standard toothpaste was 4.37 (1.72).

The values of (W2-1.5) and the RSFI for the toothpastes of the Examples were as follows.

| Example | W2 - 1.5 | RSFI |
|---|---|---|
| 1 | 2.88 (1.45) | 75 (16) |
| 2 | 3.18 (1.45) | 79 (33) |
| 3 | 3.21 (1.88) | 73 (29) |
| 4 | 3.31 (1.71) | 78 (29) |

Experiments were also conducted which showed the enhanced salivary fluoride levels after use of toothpastes of the invention. The test method used was as follows.

1. A panel of ten adults used a non-fluoride toothpaste at home for several days prior to the test and during the experimental period.
2. At the time of the test, panellists brushed their teeth with 1.5 g toothpaste for 1 minute, expectorated and then rinsed with 10 ml water for 5 seconds (twice).
3. Samples of saliva were collected immediately before toothpaste application and at regular intervals afterwards.
4. Salivary fluoride ion activities were measured using a fluoride ion specific electrode (Orion 9409) in the presence of a buffer known in the art as TISAB (total ionic strength adjustment buffer).
5. To ensure complete conversion of monofluorophosphate ions to fluoride ions before analysis, saliva samples collected within 15 minutes or toothpaste use were incubated at 37° C. overnight whilst all samples collected later were stored at room temperature for two days.
6. Individual pastes were tested at intervals of at least two full days and panellists were not allowed to eat or drink during experimental periods.

The logarithms of the salivary fluoride ion activities were plotted against time and the extrapolated zero time intercept determined from data values obtained at times equal to and greater than 60 minutes. The fluoride concentration corresponding to this intercept is referred to below as the fluoride reservoir depth (FRD) and is expressed in ppm F. The results of three different tests are indicated below.

| Toothpaste | FRD | % increase in FRD compared to: | |
|---|---|---|---|
| | | Standard | Modified Standard |
| Test 1 | | | |
| Standard | 0.069 (0.033)** | — | |
| Formulation 1 | 0.166 (0.105) | 141 | |
| Test 2 | | | |
| Standard | 0.056 (0.037) | — | 51 |
| Modified Standard* | 0.037 (0.016) | −34 | — |
| Formulation 3 | 0.063 (0.039) | 13 | 70 |
| Test 3 | | | |
| Standard | 0.066 (0.024) | — | 78 |
| Modified Standard* | 0.037 (0.021) | −44 | — |
| Formulation 2 | 0.089 (0.069) | 35 | 141 |
| Formulation 3 | 0.056 (0.028) | −15 | 51 |
| Formulation 4 | 0.054 (0.042) | −18 | 46 |

*As the Standard formulation but having a content of sodium monofluorophosphate of 0.455% corresponding to 600 ppm F, i.e. the same as that of Forumlations 2 to 4.
**The number between the brackets is the standard deviation.

Examples 5 to 8 are further examples of toothpastes of this invention.

EXAMPLE 5

| Ingredient | % |
|---|---|
| Alumina trihydrate | 50.00 |
| Sorbitol syrup (70% solution) | 29.59 |
| Sodium lauryl sulphate | 0.15 |
| Xanthan gum | 1.10 |
| Sodium monofluorophosphate | 0.76 |
| Zinc citrate trihydrate | 1.00 |
| Sodium saccharinate | 0.018 |
| Titanium dioxide | 0.50 |
| Flavour (spearmint oil) | 0.12 |
| Formalin | 0.04 |
| Water (demineralised) | to 100.00 |

EXAMPLE 6

| Ingredient | % |
|---|---|
| Alumina trihydrate | 50.00 |
| Sorbitol syrup (70% solution) | 29.28 |
| Sodium lauryl sulphate | 0.30 |
| Sodium carboxymethylcellulose | 1.00 |
| Sodium monofluorophosphate | 0.76 |
| Sodium saccharinate | 0.02 |
| Monosodium phosphate (anhydrous) | 0.31 |
| Titanium dioxide | 0.50 |
| Flavour (spearmint oil) | 0.05 |
| Water | 17.78 |

EXAMPLE 7

| Ingredient | % |
|---|---|
| Silica | 18.0 |
| Sorbitol syrup (70% solution) | 69.0 |
| Polyethylene glycol 1500 | 5.0 |
| Sodium lauryl sulphate | 0.7 |
| Sodium carboxymethylcellulose | 0.5 |
| Sodium fluoride | 0.22 |
| Sodium saccharinate | 0.06 |
| Titanium dioxide | 1.0 |
| Flavour oil | 0.4 |
| Water | to 100.0 |

EXAMPLE 8

| Ingredient | % |
|---|---|
| Silica | 22.0 |
| Sorbitol syrup (70% solution) | 50.0 |
| Polyethylene glycol 1500 | 5.0 |

-continued

| Ingredient | % |
| --- | --- |
| Sodium lauryl sulphate | 0.7 |
| Sodium carboxymethylcellulose | 0.65 |
| Sodium fluoride | 0.22 |
| Sodium saccharinate | 0.06 |
| Titanium dioxide | 1.0 |
| Flavour oil | 0.4 |
| Water | to 100.0 |

I claim:

1. A toothpaste comprising about 5 to about 75% by weight of an abrasive cleaning agent, an oral therapeutic agent which is a source of fluoride ions present in an effective amount to inhibit caries, 0.01 to 0.05% by weight of a flavouring agent, 0.002 to 0.01% by weight of a sweetening agent and 0.075 to 1.5% by weight of an anionic surfactant, the amount of said flavouring and sweetening agent being sufficiently low to reduce their normal stimulatory effect upon salivary flow.

2. A toothpaste as claimed in claim 1 wherein the abrasive agent is silica or alumina.

3. A toothpaste as claimed in claim 1 wherein the therapeutic agent is selected from the group consisting of sodium fluoride, sodium monofluorophosphate, and mixtures thereof.

4. A toothpaste as claimed in claim 1 wherein the sweetening agent is sodium saccharinate.

5. A toothpaste as claimed in claim 1 wherein the sweetening agent is selected from the group consisting of sodium saccharinate, aspartame, sodium cyclamate and thaumatin.

6. A toothpaste as claimed in claim 1 wherein the anionic surfactant is a sodium lauryl sulphate.

7. A method to reduce salivary flow in an oral cavity to effect a longer retention of fluoride ions in said oral cavity, said method comprising applying to teeth a toothpaste comprising from about 5 to 75% by weight of an abrasive cleaning agent, an effective amount of fluoride ions sufficient to inhibit carries, 0.01 to 0.6% by weight of a flavouring agent, 0.002 to 0.1% by weight of a sweetening agent and 0 to 1.5% by weight of an anionic surfactant, the amount of said flavouring and sweetening agent being sufficiently low to reduce their normal stimulatory effect upon said salivary flow.

8. A method according to claim 7 wherein the amount of flavouring agent is 0.01 to 0.5% by weight.

9. A method according to claim 7 wherein said sweetening agent is sodium saccharinate present at a level from 0.02 to 0.6%.

10. A method according to claim 7 wherein said sweetening agent is selected from the group consisting of sodium saccharinate, aspartame, sodium cyclamate and thaumatin.

* * * * *